United States Patent [19]

Solodar

[11] 3,968,147

[45] July 6, 1976

[54] ASYMMETRIC REDUCTION OF KETONES TO FORM OPTICALLY ACTIVE ALCOHOLS

[75] Inventor: Arthur John Solodar, St. Louis, Mo.

[73] Assignee: Monsanto Company, St. Louis, Mo.

[22] Filed: Oct. 29, 1974

[21] Appl. No.: 518,304

Related U.S. Application Data

[63] Continuation-in-part of Ser. No. 224,971, Feb. 9, 1972, Pat. No. 3,883,580.

[52] U.S. Cl. .......................... 260/482 C; 260/570.6; 260/584 R; 260/613 D; 260/617 C; 260/618 H; 260/618 D; 260/618 B; 260/633; 260/638 B; 252/430; 260/570.5 R
[51] Int. Cl.² ................. C07C 125/04; C07C 29/16
[58] Field of Search ............ 260/482, 617 C, 618 R, 260/618 D, 618 B, 613 D, 638 B, 482 C

[56] References Cited

FOREIGN PATENTS OR APPLICATIONS 1,138,601   1/1969   United Kingdom............ 260/617 C

*Primary Examiner*—Paul J. Killos

[57] ABSTRACT

A process for producing optically active secondary alcohols by reducing an optically inactive ketone in the presence of an optically active Group VIII metal coordination complex catalyst is disclosed. One embodiment is directed to a process for forming opticallly active aliphatic or aromatic secondary alcohols by reacting an optically inactive ketone with hydrogen in the presence of a Group VIII metal complex catalyst which contains the metal in combination with at least one optically active ligand having an optically active group attached to a phosphorous or arsenic atom.

21 Claims, No Drawings

ASYMMETRIC REDUCTION OF KETONES TO FORM OPTICALLY ACTIVE ALCOHOLS

RELATED APPLICATION

This application is a continuation-in-part of copending application Ser. No. 224,971, filed Feb. 9, 1972, now U.S. Pat. No. 3,883,580.

BACKGROUND OF THE INVENTION

An asymmetric carbon atom by commonly accepted definition is a carbon atom containing four different radicals or atoms attached to it. Compounds which contain elements of molecular dissymmetry and compounds which contain one or more asymmetric atoms in the absence of a molecular center, plane or alternating axis of symmetry are known as chiral compounds. Chiral compounds can exist in two enantiomeric or mirro image forms also called optical isomers. Samples of chiral compounds which contain equal amounts of each enantiomer are known as racemic mixtures, but if such samples contain definite but unequal portions of each enantiomer they are called partially racemic, partially resolved or optically active. Fully resolved samples of chiral compounds which contain only one enantiomer are called optically pure.

The carbon atom of the carbonyl group in a ketone cannot be asymmetric because of the doubly bonded oxygen atom attached to it. Even if the two R groups of the

ketone compound are different, the carbon atom of the carbonyl group can only contain three different groups, the R, R', and the doubly bonded oxygen, and cannot be asymmetric. When the ketone is reduced to the secondary alcohol,

the carbon atom acquires four different groups attached to it, if $R^2$ is different from $R^3$ and neither $R^2$ nor $R^3$ is hydrogen. This creates a point of asymmetry in the alcohol. Many prior art methods for producing alcohols from ketones have nevertheless produced only racemic mixtures, because of their production of equal amounts of the two stereoisomers of the secondary alcohol. To obtain a preponderance of the desired enantiomorphic form of the alcohol, the mixture has to be separated into its optical components by inefficient and often expensive methods such as distillations, crystallizations and the like.

SUMMARY OF THE INVENTION

Providing a means for producing a preponderance of a desired optical isomer of a secondary alcohol directly from the ketone without the necessity of employing any separation step in addition to the ketone reduction constitutes a principal object of this invention.

This invention relates to a method for preparing optically active secondary alcohols. Specifically, the invention relates to a method for preparing optically active secondary alcohols comprising reacting an optically inactive ketone having no asymmetric atoms of the formula

where R is different from R' and where both Rs can be any monovalent hydrocarbon group attached directly to the carbonyl group through a carbon atom, with hydrogen in the presence of an optically active catalyst which is a coordination complex comprising a. a Group VIII metal having an atomic number greater than 43, in combination with
b. at least one optically active phosphine or arsine ligand wherein the optical activity of the ligand is contained in one or more groups attached to the phosphine or arsine atom.

DESCRIPTION OF THE PREFERRED EMBODIMENTS

Secondary alcohols prepared by the process of this invention have the formula

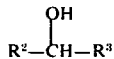

where $R^2$ and $R^3$ are different from each other and are any monovalent hydrocarbon group attached directly to the optically active carbon atom through a carbon to carbon bond, and where the * indicates the asymmetric carbon atom. The R groups of both the ketone and the alcohol can be either substituted or unsubstituted hydrocarbon groups. If substituted, the substituent groups can be halogen, amino, nitro, hydroxyl, carboxyl and cyano; phosphorous, arsenic, silicon, oxygen and sulfur atoms or groups containing said atoms; and any of a large number of other substituents recognized as capable of being present on hydrocarbon groups. Since the hydrogenation reaction which produces the alcohol acts upon the carbonyl group of the ketone, the R groups can actually be any substituted or unsubstituted hydrocarbon groups which do not interfere with the hydrogenation of the carbonyl group. The above mentioned substituent groups should therefore be considered merely as exemplary and not in any way as limiting the scope of the invention. Examples of secondary alcohols which can be prepared include 2-butanol; 2-octanol; 3-octanol; alphamethylbenzylalcohol; alpha-phenyl-4-chlorobenzyl alcohol; 1-amino-3-phenyl-2-propanol; 1-chloro-4-methyl-3-pentanol; 1-nitro-2-propanol; 1-phenyl-2-propanol; 1-amino-2-octanol; 2-methylamino-1-(3'-hydroxyphenyl)-ethanol; 3-(2'-methoxy-phenoxy)-propane-1, 2-diol; 1-isopropylamino-3-(1'-naphthoxy)-2-propanol; alphatolylphenylmethanol; 1-carbamoyloxy-3-(2'-methoxyphenoxy)-2-propanol; and 1-carbamoyloxy-3-(4'-chlorophenoxy)-2-propanol.

The ketones which are hydrogenated to produce secondary alcohols have the formula

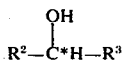

where the Rs are as described above in connection with the alcohols. In many instances, the R groups of the ketone will correspond exactly with the R groups of the secondary alcohol produced from the ketone. In other instances, the R groups of the ketone may differ from those of the alcohol produced therefrom due to the alteration of the ketone R groups during the hydrogenation reaction. As an example, a ketone R group such as —CH=$CH_2$ could be reduced by the hydrogenation reaction to form a —$CH_2CH_3$ group on the secondary alcohol. The R groups of the ketones used in this invention are further limited to groups containing no asymmetric atoms. Hence the process of this invention provides asymmetry in a product produced from a starting reactant which contains no asymmetry. Moreover, not only does the product contain a point of asymmetry, but the product is further characterized by a preponderance of one optical isomer over the other. Examples of suitable ketones include 2-butanone; 2-octanone; 3-octanone; acetophenone; 4-chlorobenzophenon; 1-amino-3-phenyl-2-propanone; 1-cloro-4-methyl- 3-pentanone; 1-nitro-2-propanone; 1-phenyl-2-propanone; 1-amino octanone-2; 2-methylamino-3'-hydroxyacetophenone; hydroxy-3-(2'-methoxyphenoxy)-2propanone; 1-isopropylamino-3-(1'-naphthoxy)-2-propanone; 2-methylbenzophenone; 1-carbamoyloxy-3-(2'-methoxyphenoxy)-2-propanone; and 1-carbamoyloxy-3-(4'-chlorophenoxy)-2-propanone.

The production of an optically active alcohol by hydrogenation of a ketone is accomplished through the use of a particular type of catalyst.

The optically active hydrogenation catalysts useful in this invention are coordination complexes comprising a Group VIII metal having an atomic number greater than 43, in combination with at least one optically active phosphine or arsine ligand wherein the optical activity of the ligand is contained in one or more groups attached to the phosphine or arsine atom.

The designation "Group VIII" refers to Group VIII of the Periodic System of the Elements. The reference to Group VIII metals having an atomic number greater than 43 is used to include ruthenium, rhodium, palladium, osmium, iridium and platinum. Preferred among the foregoing metals are ruthenium, rhodium and iridium, and most preferably rhodium. Mixtures of the foregoing metals in complex form are also useful.

The phosphine or arsine ligand can be of the formula $AR^4R^5R^6$ wherein A is phosphorous or arsenic and $R^4$, $R^5$ and $R^6$ can be hydrogen, alkyl, aryl, aralkyl, alkaryl, alkoxy, aryloxy, pyrryl, thienyl, furyl, pyridyl, piperidyl, 3-cholesteryl and other similar groups having a maximum of about 12 carbon atoms, groups such as the above which are substituted with other groups such as amino, nitro, carbonyl, carboxyl, halogen, alkoxy and aryloxy preferably having a maximum of about 4 carbon atoms.

Specific examples of substituents on the phosphorous and arsenic atoms include but are not limited to: methyl, ethyl, propyl, isopropyl, butyl and its isomers, pentyl and its isomers, hexyl and its isomers, heptyl and its isomers, octyl and its isomers, nonyl and its isomers, decyl and its isomers, undecyl and its isomers, dodecyl and its isomers, cyclopropyl, cyclobutyl, cyclopentyl, ciclohexyl, phenyl, acetoxyphenyl, methylphenyl, ethylphenyl, propylphenyl, butylphenyl, dimethylphenyl, trimethylphenyl, diethylphenyl, hydroxyphenyl, phenoxyphenyl, alpha-anisyl, 3-cholesteryl, benzyl, pyrryl, furyl, pyridyl, thienyl, piperidyl, menthyl, bornyl and pinyl.

A list of optically active phosphines and arsines which may be utilized includes but is not limited to: methylethylphosphine, methylisopropylephosphine, ethylbutylphosphine, isopropylisobutylphosphine, methylphenylphosphine, ethylphenylphosphine, propylphenylphosphine, butylphenylphosphine, phenylbenzylphosphine, phenylpyrrolephosphine, ethylisopropylisobutylphosphine, methylphenyl-4-methylpenylphosphine ethylephenyl-4-methylphenylphosphine, methylisopropylphenylphosphine ethylphenyl-2,4,5-trimethylphenylphosphine, phenylbenzyl-4-dimethyl-aminophenylphosphine, phenylpyridylmethylphosphine, phenylcyclopentylethylphosphine, cyclohexylmethylisopropylphosphine, o-methoxy-phenylmethylphenylphosphine, o-methoxyphenylcyclohexylmethylphosphine and the arsenic analogs of the above.

Examples of suitable ligands that are useful in making catalysts in the present invention include optically active phosphines and arsines containing at least one phenyl group that has a substituent in the ortho position such as hydroxy; alkoxy having at least one carbon atom and a maximum of twelve carbon atoms; and aryloxy. Good results have been obtained with methylphenyl-o-anysylphosphine and methylcyclohexyl-o-anisylphosphine as ligands.

Optical activity of the metal coordination complexes of this invention resides in the phosphine or arsine ligand. This optical activity may result either from having three different groups on the phosphorous or arsenic atom or by having an optically active group attached to the phosphorous or arsenic atom. Although only one optically active group or ligand is required in the coordination metal complex catalyst, it is preferred, for ease of preparation, that all ligands of the types described below be the same.

Illustrative coordination metal complexes can be represented by the formula $M^1 X_n L_3$ or $M^2 X_2 L_2$ wherein $M^1$ is rhodium, iridium, ruthenium or osmium; $M^2$ is palladium or platinum; X is hydrogen or halogen, L is the phosphine or arsine ligand as previously defined and $n$ is the integer one or three.

In the above coordination metal complex formulae, only one ligand (L) has to be optically active in order for the process of the reaction to be operable. When the optical activity of the ligand resides in having an optically active group attached to the phosphorous or arsenic atom, there only has to be one such group, and the other two groups may be the same or inactive. In this instance, only one of the groups $R^4$, $R^5$ or $R^6$ has to be optically active, the remaining two groups may be identical or inactive.

In the above coordination metal complex formulae, two of the ligands (L) may actually be chemically bonded together to form a bidentate ligand. When the bidentate ligand is optically active it may have one or more centers of chirality. In this instance the remaining R groups may be optically active or inactive.

Catalysts which may be used include, but are not limited to, coordination metal complexes of the following formulae. In the formulae, an asterisk indicates asymmetry, and therefore optical activity. The asterisk denotes the asymmetric atom or disymmetric group. As an example: A* indicates the phosphorous or arsenic is asymmetric. Absence of an asterisk indicates no optical activity.

(i) $M^1X(A^*R^4R^5R^6)_3$
(ii) $M^1X(A^*R^4R^5R^6)_2AR^4R^5R^6)$
(iii) $M^1X(A^*R^4R^5R^6)(AR^4R^5R^6)_2$ (iv) $M^1X(AR^{*4}R^5R^6)_3$
(v) $M^1X(AR^{*4}R^5R^6)_2(AR^4R^5R^6)$
(vi) $M^1X(AR^{*4}R^5R^6)(AR^4R^5R^6)_2$
(vii) $M^1X_3(A*R^4R^5R^6)_3$
(viii) $M^1X_3(A*R^4R^5R^6)_2(AR^4R^5R^6)$
(ix) $M^1X_3(A*R^4R^5R^6)(AR^4R^5R^6)_2$
(x) $M^1X_3(AR^{*4}R^5R^6)_3$
(xi) $M^1X_3(AR^{*4}R^5R^6)_2(AR^4R^5R^6)$
(xii) $M^1X_3(AR^{*4}R^5R^6)(AR^4R^5R^6)_2$
(xiii) $M^2X_2(A*R^4R^5R^6)_2$
(xiv) $M^2X_2(A*R^4R^5R^6)(AR^4R^5R^6)$
(xv) $M^2X_2(AR^{*4}R^5R^6)_2$
(xvi) $M^2X_2(AR^{*4}R^5R^6)(AR^4R^5R^6)$ where $M^1$, $M^2$, X, A, $R^4$, $R^5$, and $R^6$ are as previously defined.

It is understood that in the above illustrated list of catalysts, the dissymmetric group can be $R^4$, $R^5$ or $R^6$ and is not restricted to any one group. In addition, there may be a combination of moieties attached to the metal.

It should be understood that the above described formulae represent not only the coordination metal complexes that contain two or three ligands, as in the formulae $M^2X_2L_2$ or $M^1X_nL_3$ respectively, but also represent those coordination metal complexes wherein the number of ligand-metal coordination bonds are described by the number of L's in the formula and wherein these bonds are provided by polydentate type ligands. For instance, although there may be only two ligands in a particular coordination metal complex, the formula $M^1X_nL_3$ still represents the complex if one of the two ligands is bidentate, i.e., it provides two coordination bonds. Likewise the formula $M^1X_nL_3$ also represents those complexes wherein there is only one ligand present if that ligand is tridentate, i.e., it provides three coordination bonds.

Catalysts which are soluble in the starting reactants or some suitable solvent which can be used with the starting reactants are referred to as homogeneous catalysts and constitute one preferred embodiment of this invention. Another form of catalyst useful herein is bonded to some non-soluble phase such as an ion-exchange resin, which is then contacted with the ketone reactant, thereby providing the necessary thorough contact between catalyst and reactants.

It has been found that excellent yields of desired enantiomorphs can be achieved not only with the above described optically active hydrogenation catalysts, but can also be achieved when the hydrogenation is carried out in the presence of a catalyst that comprises a solution of a metal compound where the metallic component is rhodium, iridium, ruthenium, osmium, palladium or platinum, and at least one equivalent of a phosphine and/or arsine ligand per mole of metal, provided that the ligand is optically active. For instance, the catalyst can be prepared in situ by dissolving a soluble metal compound in a suitable solvent together with a ligand wherein the ratio of ligand to metal is at least one equivalent of ligand per mole of metal, preferably two equivalents of ligand per mole of metal. Likewise, it has been found that the catalyst can be formed in situ by adding a soluble metal compound to the reaction mass together with the addition of the proper amount of the optically active ligand to the reaction mass either before or during hydrogenation.

The preferred metal used herein is rhodium. Soluble rhodium compounds that can be utilized include rhodium trichloride hydrate, rhodium tribromide hydrate, rhodium sulfate, organic rhodium complexes with ethylene, propylene, etc., and bis olefins such as 1,5-cyclooctadiene and 1,5-hexadiene, bicyclo-[2.2.1]-hepta-2,5-diene and other dienes which can form bidentate ligands, or an active form of metallic rhodium that is readily solubilized.

Cationic coordination metal complexes containing two equivalents of phosphine or arsine or the equivalents of a bidentate phosphine or arsine per mole of metal and a chelating bis-olefin can be used as the catalysts in the present invention. For instance, using the organic rhodium complexes, as described above, one can prepare such cationic coordination rhodium complexes by slurrying the organic rhodium complex in an alcohol, such as ethanol, adding two equivalents of the optically active phosphine or arsine or the equivalents of a bidentate phosphine or arsine so that an ionic solution is formed followed by the addition of a suitable anion such as, for instance, tetrafluoroborate, tetraphenylborate or any other anion that will result in the precipitation or crystallization of a solid cationic coordination metal complex either directly from the solution or upon treatment in an appropriate solvent.

For instance, exemplary cationic coordination metal complexes are: rhodiumnorbornadiene (+)-2,3-O-isopropylidene-1,4-bis-(diphenylphosphino)-butane tetrafluoroborate, 1,5-cyclooctadiene-bis(neomenthyldiphenylphosphine) rhodium tetrafluoroborate and norbornadiene-bis-(2-hexyldiethylphosphine) rhodium hexafluorophosphate, 1,5-cyclooctadiene-bis(methylcyclohexyl-o-anisylphosphine) rhodium tetrafluoroborate, 1,5-cyclooctadiene-bis-(methylcyclohexyl-o-anisylphosphine) rhodium tetraphenylborate and bicyclo-[2.2.1]-hepta-2,5-diene-bis (methylcyclohexyl-o-anisylphosphine) rhodium tetrafluoroborate.

Without prejudice to the present invention it is thought that the charged components, referred to hereinabove as catalysts, are actually catalyst precursors and that upon contact with hydrogen the precursors are converted to an active catalytic form. This conversion, can, of course, be carried out during the actual hydrogenation of the ketone or can be accomplished by subjecting the catalyst (or precursor) to hydrogen prior to addition to the ketone material to be hydrogenated.

The hydrogenation reaction is usually conducted in a solvent, such as benzene, ethanol, toluene, cyclohexane, and mixtures of these solvents. Almost any aromatic or saturated alkane or cycloalkane solvent, which is inactive to the hydrogenation conditions of this reaction, can be used. Carboxylic acids, esters, anhydrides, amides, and ethers can also be employed. Since the hydrogenation process of this invention has been found to be specific, solvents such as nitrobenzene can also be utilized. Preferred solvents are alcohols such as methanol or ethanol, and carboxylic acids such as acetic acid. Alternatively, the reaction can be carried out using only neat reactants.

The catalyst can be added to the solvent or reactants either as a compound per se or as its components which then form the catalyst in situ. When the catalyst is added as its components it may be added prior to, or at the same time, as the ketone. Components for the preparation of the catalyst in situ are the soluble metal compound and the optically active phosphine or arsine ligand. The catalyst can be added in any effective catalytic amount and generally in the range of about 0.0001% to about 5% by weight of contained metal based on the ketone reactant. A preferred concentration range is from about 0.0002% to about 0.2% of the ketone.

It has been found that the process of this invention is preferably carried out in the presence of an optically active phosphine or arsine ligand wherein the ligand is present in a ratio of about 1.0 or less up to about 200 or more equivalents of ligand per mole of metal, although the range of about 1.5 to about 2.9 and more preferably about 2.0 equivalents has been found to be especially useful; however when bidentate ligands are employed these equivalents values are reduced by about 50%. In practice it is preferred to have the optically active catalyst in a solid form for purposes of handling and storage. It has been found that these results can be obtained with solid, cationic coordination metal complexes.

Within practical limits, means should be provided so as to avoid contacting the catalyst or reaction mass with oxidizing materials. In particular, care should be taken so as to avoid contact with oxygen. It is preferred to carry out the hydrogenation reaction preparation and actual reaction in gases (other than $H_2$) that are inert to both reactants and catalysts such as, for instance nitrogen or carbon dioxide.

After addition of the components to the solvent, hydrogen is added to the mixture until about 1 to about 5 times the mole quantity of the ketone or an amount necessary to complete the hydrogenation to the point desired has been added. The pressure of the system will necessarily vary since it will be dependent upon the type of ketone, type of catalyst, size of hydrogenation apparatus, amount of components and amount of solvent. Lower pressures, including atmospheric and sub-atmospheric pressure, can be used as well as higher pressures. Examples set forth below have used pressures in the range of about 3 to about 12 atmospheres, although pressures as high as 40 to 50 atmospheres can be used.

Reaction temperatures may be in the range of about −20° to about 110°C. Higher temperatures may be used but are normally not required and may lead to an increase of side reactions such as the racemization of the optically active ligands. Preferred temperatures are about 40° to 100°C.

One additive sometimes used in the hydrogenation reaction is water. A small amount of water in the range of 1% or less of the reactants acts as a rate accelerator and can therefore be useful in the practice of this invention. It has been found, however, that the presence of water may reduce the optical purity of the alcohol product. That is, the catalyzed hydrogenation reaction of this invention, if carried out under anhydrous conditions, may produce alcohols with a greater optical purity than is obtained when small amounts of water are present. It has been found that as little as 0.05% water has the above-mentioned effects on reaction rate and product optical purity.

Upon completion of the reaction which is determined by conventional means, the solvent is removed and the products and catalysts separated by conventional means.

Many naturally occurring products and medicaments exist in an optically active form. In these cases only one of the L or D forms is usually effective. Synthetic preparation of these compounds in the past has required an additional step of separating the products into its enantiomorphs. This process is expensive and time consuming. The process of the present invention permits the formation of optically active products thus eliminating much of the time consuming and expensive separation of enantiomorphs while improving the yield of desired enantiomorphs and reducing the yield of unwanted enantiomorphs.

The following examples are given to illustrate in detail how the process of this invention is carried out. It is to be understood that the specific details given in the examples are not to be construed as limiting the scope of the invention. In the following examples "parts" are by weight unless otherwise indicated. In the examples the % optical purity is determined by the following equation (it is understood that the optical activities expressed as the specific rotations are measured in the same solvent):

% Optical Purity = observed opitcal activity of the mixture × 100 / optical activity of pure enantiomorph

EXAMPLE 1

Into a 3 ounce glass pressure bottle are placed 66.4 milligrams of [Rh(norbornadiene)Cl]$_2$, 98 milligrams of optically active phenylmethyliso-propylphosphine ($[\alpha]_D^{25}$ = +11.0°[toluene, $c$ = 0.50]), 8.2 grams of 2-octanone and 0.1 ml water. The bottle is flushed by filling 4 times for at least 30 seconds with at least 30 psig hydrogen and then venting the gas and is then filled to 30 psig hydrogen. The bottle is warmed to 60°C and the contents stirred for 21 hours. The reaction mass is distilled to afford a mixture of 2-octanone and 2-octanol. The 2-octanol has $[\alpha]_D^{25}$ = −0.60°, optical purity = 5.9%.

EXAMPLE 2

Into a 3 ounce glass pressure bottle are placed 49 milligrams of [Rh(1,5-cyclooctadiene) (o-anisylcyclohexylmethylphosphine)$_2$]BF$_4$ (optical purity of phosphine ~95%), 8.2 grams of 2-octanone, 0.20 ml water, and 10 ml iso-butyric acid. The bottle is flushed 4 times as in Examle 1 and then filled to 70 psig hydrogen. The bottle is warmed to 72°C and the contents stirred for 19.5 hours. The reaction solution is then dissolved in 50 ml chloroform, washed 3 times with 50 ml 5% aqueous sodium hydroxide solution and once with 20 ml water and then dried with anhydrous magnesium sulfate. Distillation affords a mixture of 2-octanol and 2-octanone. The 2-octanol has $[\alpha]_D^{25}$ = −1.148°, optical purity = 11.2%.

EXAMPLE 3

Into a 3 ounce glass pressure bottle are placed 1.15 grams C$_6$H$_5$COCH$_2$NHCH$_2$C$_6$H$_5$, 18 milligrams of [Rh(1,5-cyclooctadiene) (o-anisylcyclohexylmethylphosphine)$_2$]BF$_4$ (phosphine optical purity ~95%), 20 ml absolute ethanol and 0.20 ml water. The bottle is flushed and filled as in Example 1 with 60 psig hydrogen. The bottle is warmed to 55°C and the contents stirred for 3.25 hours. The solvent is removed by distillation and the product, C$_6$H$_5$CHOHCH$_2$NHCH$_2$C$_6$H$_5$, isolated by extraction into hot hexane and crystallization from cold hexane. It has $[\alpha]_D^{25}$ = −1.7° (absolute EtOH, $c$ = 0.66).

EXAMPLE 4

Into a 3 ounce glass pressure bottle are placed 173 milligrams of [Rh(norbornadiene) (iso-propylmethylphenylphosphine)$_2$]BF$_4$ ($[\alpha]_D^{25}$ = +11.0° for the phosphine), 8.2 grams of 2-octanone, 5 ml absolute ethanol, and 0.12 ml water. The bottle is flushed and filled with hydrogen as in Example 1 to 43 psig hydrogen. The bottle is warmed to 75°C and the contents stirred for 3.5 hours. The reaction mass is distilled to afford almost pure 2-octanol, $[\alpha]_D^{25} = +0.15°$, optical purity = 1.5%.

EXAMPLE 5

Into a 3 ounce glass pressure bottle are placed 75 milligrams of [Rh(norbornadiene)Cl]$_2$, 7.7 grams of acetophenone, 2 ml absolute ethanol, 113 milligrams iso-propylphenylmethylphosphine ($[\alpha]_D^{25} = +11.0°$) and 0.12 ml water. The bottle is flushed and filled with hydrogen as in Example 1 to 30 psig hydrogen. The bottle is warmed to 60°C and the contents stirred for 43 hours. Distillation of the reaction mass affords a mixture of acetophenone and α-methylbenzyl alcohol. The α-methylbenzyl alcohol has $[\alpha]_D^{25} = +4.87°$, optical purity = 11.4%.

EXAMPLE 6

Into a 3 ounce glass pressure bottle are placed 180 milligrams of [Rh(norbornadiene) (iso-propylphenylmethylphosphine)$_2$]BF$_4$ ($[\alpha]_D^{25} = +11.0°$ for the phosphine), 7.7 grams of acetophenone, 3 ml absolute ethanol, and 0.12 ml water. The bottle is flushed and filled with hydrogen as in Example 1 to 30 psig. The bottle is warmed to 60°C and the contents stirred for 5 hours. Distillation of the reaction mass affords pure α-methylbenzyl alcohol, $[\alpha]_D^{25} = -1.78°$, optical purity = 4.2%.

EXAMPLE 7

Into a 3 ounce glass pressure bottle are placed 73.6 milligrams of [Rh(norbornadiene)Cl]$_2$, 178 milligrams of phenylmethyl n-decylphosphine (optical purity = 76%), 7.7 grams of acetophenone, 2 ml absolute ethanol, and 0.12 ml water. The bottle is flushed and filled with hydrogen as in Example 1 to 30 psig. The bottle is warmed to 65°C and the contents stirred for 18 hours. The reaction mass is distilled to afford a mixture of acetophenone and α-methylbenzyl alcohol. The α-methylbenzyl alcohol has $[\alpha]_D^{25} = 3.5 + 1.47°$, optical purity = 3.5%.

EXAMPLE 8

Into a 3 ounce glass pressure bottle are placed 49 milligrams of [Rh(1,5-cyclooctadiene) (o-anisylcyclohexylmethylphosphine)$_2$]BF$_4$ (phosphine optical purity ~95%), 10.2 grams phenylacetone and 10 ml iso-butyric acid. The bottle is flushed by filling 4 times for at least 30 seconds with at least 30 psig hydrogen, followed by venting the gas and a final filling with hydrogen to 70 psig. The bottle is warmed to 80°C and stirred for 24 hours. The reaction mass is dissolved in 50 ml chloroform, washed three times with 50 ml 5% aqueous sodium hydroxide solution, once with 20 ml water and then dried over anhydrous magnesium sulfate. Distillation affords a mixture of 1-phenyl-2-propanol and phenylacetone. The 1-phenyl-2-propanol has $[\alpha]_D^{25} = -5.31°$, optical purity = 19.9%.

EXAMPLE 9

Into a 3 oz. glass pressure reactor are placed 40 milligrams of [Rh(norbornadiene)Cl]$_2$, 86 milligrams of optically active (−) 2,3-O-isopropylidene-1,4-bis-(diphenylphosphino)-butane, 10.0 milliliters of methyl acetoacetate, 10 milliliters of ethanol and 0.1 milliliters of water. The contents are stirred for 3 minutes, and then stirred and sparged with nitrogen for 20 minutes. The bottle is flushed by filling 5 times for at least two minutes with 155 psig hydrogen and then venting the gas and then is filled to 155 psig hydrogen. The bottle is warmed to 75°C and the contents stirred for 20 hours. The reaction mass is distilled to afford a mixture of methylacetoacetate and methyl 3-hydroxybutyrate. The mixture has α=+0.289° optical purity of contained methyl/3-hydroxybutyrate=9%.

EXAMPLE 10

Into a 3 oz. glass pressure reactor are placed 42.5 milligrams of [Rh(norbornadiene)Cl]$_2$, 119 milligrams of optically active neomenthyldiphenylphosphine, 10.0 milliliters of methyl acetoacetate, 10 milliliters of ethanol and 20 microliters of water. The contents are stirred and sparged with nitrogen for 20 minutes and the bottle is then flushed by filling with 135 psig hydrogen 5 times for at least 2 minutes. Finally the bottle is filled with 155 psig hydrogen and heated at 80°C while the contents are stirred for 20 hours. The reaction mass is distilled to afford a mixture of methyl acetoacetate and methyl 3-hydroxybutyrate. The contained methyl 3-hydroxybutyrate has $[\alpha]_D^{RT} = 1.60$ (H$_2$O, C=0.55); optical purity = 6%. EXAMPLE 11

A solution containing suitable catalyst components is prepared as follows. To a nitrogen sparged solution of 47 milligrams at Ag PF$_6$ in 2 milliliters of ethanol is added, under a nitrogen blanket, a slurry of 43 milligrams of [Rh(norbornadiene)Cl]$_2$ in 2 milliliters of ethanol. After stirring for 5 minutes an argon sparged solution of 119 milligrams of optically pure neomenthyldiphenylphosphine in 7 milliliters of ethanol is added via syringe. This mixture is filtered through a fiber glass filter under nitrogen pressure to afford a filtrate solution of catalyst components free of chloride and silver.

To this filtrate is added 10.0 milliliters of methyl acetoacetate. This solution is placed in a 3 oz. glass pressure reactor and sparged with argon for 15 minutes. The bottle is then flushed by filling with 155 psig hydrogen 5 times for at least 2 minutes. The bottle is filled with 155 psig hydrogen and heated to 80°C. The contents are stirred for 20 hours.

The reaction mass is then distilled to afford pure methyl 3-hydroxybutyrate $[\alpha]_D^{RT} = -1.08°$ (H$_2$O, C=3.16); optical purity = 4.2%.

EXAMPLE 12

To a 3 oz. glass pressure reactor are charged 10.0 milliliters methyl acetoacetate, 140 milligrams of rhodium norbornadiene (+)-2,3-O-isopropyliden-1,4-bis-(diphenylphosphino)-butane tetrafluoroborate, 10 mililiters of ethanol and 20 microliters of water. The contents are sparged with nitrogen for 20 minutes and the bottle is then flushed by filling with 135 psig hydrogen 5 times for at least 2 minutes. Finally the bottle is filled with 155 psig hydrogen and the contents stirred for 22 hours at 80°C. The reaction mass is distilled to afford a mixture of methyl acetoacetate and methyl 3-hydroxybutyrate. The contained methyl 3-hydroxybutyrate has $[\alpha]_D^{RT} = +1.0°$ (H$_2$O, C=2.70); optical purity = 4%.

EXAMPLE 13

To a 3 oz. glass pressure reactor are charged 10.0 milliliters of phenylacetone, 88 milligrams of [Rh(norbornadiene)Cl]$_2$, 190 milligrams of (+) -2,3-O-isopropylidene-1,4-bis-(diphenylphosphino)-butane and 10 milliliters of isobutyric acid. The contents are sparged with nitrogen for 20 minutes and the bottle is flushed by filling with hydrogen 5 times at 135 psig for 2 minutes. Finally, the bottle is filled with 135 psig hydrogen and heated to 70°C while the contents are stirred for 18 hours. The reaction mass is distilled to afford a mixture of phenylacetone and 1-phenyl-2-propanol which has $[\alpha]_D^{RT} = -0.703°$ (neat); optical purity = 2.5%.

EXAMPLE 14

In a 3 oz. glass pressure reactor are placed 10.0 milliliters of 2-octanone, 74 milligrams of [Rh(norbornadiene)Cl]$_2$, 160 milligrams of optically pure (+)-2,3-O-isopropylidene-1,4-bis-(diphenylphosphino)-butane and 0.1 milliliter of water. The contents are sparged with nitrogen for at least 20 minutes. The bottle is flushed by filling with 135 psig hydrogen 5 times for at least 2 minutes and is then filled with 85 psig hydrogen. The bottle is heated to 70°C while the contents are stirred for 17 hours. The reaction mass is then cooled, mixed with 25 milliliters of ether and a few grams of magnesium sulfate and filtered. The filtrate is distilled to afford a mixture of 2-octanone and 2-octanol. The contained 2-octanol has $[\alpha]_D^{25} = +0.33°$ (neat); optical purity = 3.2%.

What is claimed is:

1. A process for preparing an optically active secondary alcohol comprising reacting an optically inactive ketone having no asymmetric atoms of the formula

where R is different from R'; and where both Rs can be any substituted or unsubstituted monovalent hydrocarbon group attached directly to the carbonyl group through a carbon atom, with hydrogen in the presence of an optically active catalyst whch is a coordination complex comprising
   a. a Group VIII metal having an atomic number greater than 43, in combination with
   b. at least one optically active phosphine or arsine ligand wherein the optical activity of the ligand is contained in one or more groups attached to the phosphine or arsine atom.

2. A process according to claim 1 wherein the optical activity of said attached groups results from chirality at a carbon atom.

3. A process according to claim 1 where the Group VIII metal is ruthenium, rhodium or iridium.

4. A process according to claim 1 where the Group VIII metal is rhodium.

5. A process according to claim 1 wherein at least one of said optically active ligands is a phosphine ligand.

6. A process according to claim 1 wherein all of said ligand is a phosphine ligand.

7. A process according to claim 1 wherein the ratio of optically active phosphine or arsine ligand is from about 1.5 to about 2.9 equivalents of ligand per mole of said Group VIII metal.

8. A process according to claim 7 wherein said Group VIII metal is ruthenium, rhodium or iridium.

9. A process according to claim 7 wherein said Group VIII metal is the metallic component in a coordination metal complex containing two equivalents of phosphine or arsine ligand per mole of metal.

10. A process according to claim 9 wherein said optically active catalyst contains two olefinic ligands per mole of metal in addition to the two phosphine or arsine ligands.

11. A process according to claim 1 wherein the ratio of optically active bidentate phosphine or arsine ligand is from about 0.75 to about 1.45 equivalents of ligand per mole of said Group VIII metal.

12. A process according to claim 1 wherein said optically active catalyst is formed in situ.

13. A process according to claim 1 wherein said optically active catalyst is a coordination complex of the formula a. $M^1X_nL_3$ or b. $M^2X_2L_2$ where $M^1$ is rhodium, ruthenium, iridium or osmium; $M^2$ is palladium or platinum; X is hydrogen or halogen; n is the integer one or three; and L is a phosphine or arsine ligand, provided that at least one L group is optically active.

14. A process according to claim 1 wherein said optically active catalyst is a solution of said Group VIII metal and said ligand.

15. A process according to claim 1 wherein the R groups of said ketone are substituted monovalent hydrocarbon groups.

16. A process according to claim 1 wherein said optically active secondary alcohol is 2-methylamino-1-(3'-hydroxyphenyl)-ethanol.

17. A process according to claim 1 wherein said optically active secondary alcohol is 3-(2'-methoxyphenoxy)-propane-1,2-diol.

18. A process according to claim 1 wherein said optically active secondary alcohol is 1-isopropylamino-3-(1'-naphthoxy)-2-propanol.

19. A process according to claim 1 wherein said optically active secondary alcohol is o-tolylphenylmethanol.

20. A process according to claim 1 wherein said optically active secondary alcohol is 1-carbamoyloxy-3-(2'-methoxyphenoxy)-2-propanol.

21. A process according to claim 1 wherein said optically active secondary alcohol is 1-carbamoyloxy-3-(4'-chlorophenoxy)-2-propanol.

* * * * *